(12) United States Patent
Gorsek

(10) Patent No.: US 7,476,404 B2
(45) Date of Patent: Jan. 13, 2009

(54) COMPOSITION FOR TREATMENT OF BONE LOSS

(76) Inventor: Wayne F. Gorsek, 2055 High Ridge Rd., Boynton Beach, FL (US) 33426

( * ) Notice: Subject to any disclaimer, the term of this patent is extended or adjusted under 35 U.S.C. 154(b) by 0 days.

(21) Appl. No.: 11/785,797

(22) Filed: Apr. 20, 2007

(65) Prior Publication Data

US 2008/0260862 A1 Oct. 23, 2008

(51) Int. Cl.
| | |
|---|---|
| *A61P 19/00* | (2006.01) |
| *A61P 3/02* | (2006.01) |
| *A01K 31/69* | (2006.01) |
| *A61K 33/22* | (2006.01) |
| *A61K 31/59* | (2006.01) |
| *A61K 33/06* | (2006.01) |
| *A61K 31/122* | (2006.01) |
| *A01N 55/08* | (2006.01) |
| *A01N 45/00* | (2006.01) |
| *A01N 59/06* | (2006.01) |
| *A01N 39/00* | (2006.01) |

(52) U.S. Cl. ............... 424/657; 424/602; 424/610; 426/73; 514/64; 514/167

(58) Field of Classification Search ............... 424/657, 424/602, 610; 426/73; 514/64, 167
See application file for complete search history.

(56) References Cited

U.S. PATENT DOCUMENTS

| 6,881,419 B2 * | 4/2005 | Lovett ............... 424/439 |
| 2004/0197430 A1 * | 10/2004 | Meyrowitz ............... 424/756 |

* cited by examiner

*Primary Examiner*—Andriae M Holt
(74) *Attorney, Agent, or Firm*—Hoffman, Wasson & Gitler

(57) ABSTRACT

The composition set forth provides for the treatment of bone loss and osteoporosis. The formulation combines Vitamin D; Calcium Citrate Malate; Potassium Citrate; Magnesium; Boron and Vitamin K. Each component has an effect on its own combined with a synergistic effect with the other components.

1 Claim, No Drawings

COMPOSITION FOR TREATMENT OF BONE LOSS

BACKGROUND OF THE INVENTION

Bones are living tissue with hard outer shells and "spongy" inner cores. They constantly replenish themselves daily by replacing old cells (osteoclasts) with new ones (osteoblasts). This process of new bone formation slows over time, and bones become at risk for losing density, becoming fragile and breaking.

Many factors can contribute to osteoporosis, including the aging process (especially in women after menopause), inadequate exercise, dietary errors or deficiencies, and effects of certain drugs. Homeopathic remedies will not completely reverse existing bone loss, but can bring the body into better balance and help its minerals and nutrients be used efficiently. Remedies are also helpful for aching bones and prevention or healing of fractures.

SUMMARY OF THE INVENTION

The composition set forth provides for the prevention and treatment of bone loss and osteoporosis. The formulation combines Vitamin D; Calcium Citrate Malate; Potassium Citrate; Magnesium; Boron and Vitamin K. Each component has an effect on its own combined with a synergistic effect with the other components.

DETAILED DESCRIPTION OF THE INVENTION

The composition has the following components in the listed ranges:

| | |
|---|---|
| Vitamin D | 70-20,000 IU |
| Calcium Citrate Malate | 50-5,000 mg |
| Potassium Citrate | 50-5,000 mg |
| Magnesium | 40-4,000 mg |
| Boron | 0.3-30 mg |
| Vitamin K | 30 mcg-100 mg |

One preferred embodiment of the invention has the following amounts of each component:

| | |
|---|---|
| Vitamin D | 700 IU |
| Calcium Citrate Malate | 500 mg |
| Potassium Citrate | 500 mg |
| Magnesium | 400 mg |
| Boron | 3 mg |
| Vitamin K | 300 mcg |

Vitamin D increases absorption of calcium and supports bone and immune health.

Calcium citrate is a combination of calcium and citric acid (from citrus fruit). It is easily digested and a well-absorbed form of calcium. Calcium is important for may aspects of health, but is crucial to the growth and maintenance of bones and teeth. Calcium is stored in the bones and teeth and works as a bank that the body draws from when needed. Insufficient intake of the mineral through diet can lead to depleted stores, increasing risk for developing bone-debilitating conditions such as osteoporosis. Calcium assists with nerve transmission and muscle contraction. It helps with the maintenance of healthy blood pressure, cholesterol levels, women's monthly mood fluctuations and weight management. Calcium citrate is two and one-half times better absorbed than calcium carbonate among postmenopausal women between the ages of 45 and 80. Calcium citrate also produced a higher peak calcium level in the blood. Potassium citrate is a combination of Potassium and citric acid (from citrus fruit). Potassium citrate is a potent, hypoallergenic source of potassium and the preferred form for absorption.

Magnesium is important for many systems in the body especially the muscles and nerves. Magnesium citrate also increases water in the intestines, which may induce defecation.

Boron aids the body in retaining calcium in the bones, which is especially important for postmenopausal Women. Boron also has an anabolic effect and is used by bodybuilders Vitamin K is required for proper bone formation and blood-clotting. Vitamin K can be found in leafy green vegetables, such as spinach and broccoli, and in oils, such as soybean oil.

I claim:

1. A composition for the treatment of bone loss and osteoporosis, comprising

| | |
|---|---|
| Vitamin D | 700 IU; |
| Calcium Citrate Malate | 500 mg; |
| Potassium Citrate | 500 mg; |
| Magnesium | 400 mg; |
| Boron | 3 mg; and |
| Vitamin K | 300 mcg. |

* * * * *